(12) United States Patent
Tonelli et al.

(10) Patent No.: US 8,513,471 B2
(45) Date of Patent: Aug. 20, 2013

(54) PROCESS FOR THE MANUFACTURE OF POLYOL PERFLUOROPOLYETHER DERIVATIVE

(75) Inventors: Claudio Tonelli, Sesto San Giovanni (IT); Graziano Giuseppe Vezzulli, Milan (IT); Rosaldo Picozzi, Cesate (IT); Piero Gavezotti, Milan (IT); Antonella Di Meo, Caronno Pertusella (IT)

(73) Assignee: Solvay Solexis S.p.A., Bollate (IT)

( * ) Notice: Subject to any disclaimer, the term of this patent is extended or adjusted under 35 U.S.C. 154(b) by 542 days.

(21) Appl. No.: 12/681,151

(22) PCT Filed: Oct. 3, 2008

(86) PCT No.: PCT/EP2008/063278
§ 371 (c)(1),
(2), (4) Date: Apr. 1, 2010

(87) PCT Pub. No.: WO2009/043928
PCT Pub. Date: Apr. 9, 2009

(65) Prior Publication Data
US 2010/0240930 A1 Sep. 23, 2010

(30) Foreign Application Priority Data
Oct. 5, 2007 (EP) .................................. 07117991

(51) Int. Cl.
*C07C 41/26* (2006.01)
*C07C 43/12* (2006.01)

(52) U.S. Cl.
CPC .............. *C07C 41/26* (2013.01); *C07C 43/126* (2013.01); *C10M 2211/063* (2013.01)
USPC ............ 568/615; 568/619; 568/677; 508/582

(58) Field of Classification Search
None
See application file for complete search history.

(56) References Cited

U.S. PATENT DOCUMENTS

| 3,242,218 | A | | 3/1966 | Miller |
| 3,442,942 | A | | 5/1969 | Sianesi et al. |
| 3,650,928 | A | | 3/1972 | Sianesi et al. |
| 3,665,041 | A | | 5/1972 | Sianesi et al. |
| 3,810,874 | A | | 5/1974 | Zollinger et al. |
| 3,847,978 | A | | 11/1974 | Sianesi et al. |
| 4,113,772 | A | | 9/1978 | Lagow et al. |
| 4,523,039 | A | | 6/1985 | Lagow et al. |
| 4,897,385 | A | * | 1/1990 | Wissner et al. .................. 514/77 |
| 5,246,588 | A | | 9/1993 | Tonelli et al. |
| 5,262,057 | A | | 11/1993 | Tonelli et al. |
| 5,910,614 | A | | 6/1999 | Turri et al. |
| 7,888,536 | B2 | * | 2/2011 | Davis et al. .................... 568/622 |
| 2003/0100454 | A1 | | 5/2003 | Osawa et al. |
| 2004/0072034 | A1 | * | 4/2004 | Shimokawa et al. ... 428/694 TF |
| 2004/0092406 | A1 | | 5/2004 | Osawa et al. |
| 2005/0170136 | A1 | | 8/2005 | Shimokawa et al. |

FOREIGN PATENT DOCUMENTS

| EP | 148482 A2 | 7/1985 |
| EP | 1372141 A1 | 12/2003 |

OTHER PUBLICATIONS

Turri Stefano et al. "End Group Chemistry of Fluoro-Oligomers: Highly Selective Syntheses of Diepoxy, Diallyl, and Tetraol Derivatives" Journal of Polymer Science, Part A : Polymer Chemistry, 1996, vol. 34, p. 3263-3275, John Wiley & Sons, Inc.
Schicchitano Massimo et al. "Synthesis and characterization of low-viscosity fluoropolyether-based segmented oligomers", Die Angewandte Makromoleculare Chemie, 1995, vol. 231, No. 4000, p. 47-60, Hüthig & Wepf Verlag, Zug.
Turri Stefano et al. "NMR of Perfluoropolyether Diols and Their Acetal Copolymers", Macromolecules, 1995, vol. 28, p. 7271-7275, American Chemical Society.

* cited by examiner

*Primary Examiner* — Rosalynd Keys
(74) *Attorney, Agent, or Firm* — Arent Fox LLP

(57) ABSTRACT

A process for the manufacture of a polyol (per)fluoropolyether derivative comprising:
1. reacting at least one triol having two protected hydroxyl functions and a free hydroxyl group with an activating agent, to yield an activated protected triol;
2. reacting the activated protected triol with a functional (per)fluoropolyether derivative of formula:

$$T_2-O-R_f-T_1,$$

wherein:
$R_f$ represents a fluoropolyoxyalkene chain which is a fluorocarbon segment comprising ether linkages in main chain;
$T_1$ and $T_2$, equal to or different from each other, are independently selected from
non-functional groups of formula:

$$-CF_3, -CF_2-CF_3, -CF_2Cl, -CF_2CF_2Cl,$$
$$-CF_2-COF, -COF: \text{ and}$$

functional hydroxyl groups comprising at least one hydroxyl group, with the provisio that at least one of $T_1$ and $T_2$ is a functional hydroxyl group as above detailed to yield a protected polyol (per)fluoropolyether derivative; and
3. deprotecting the protected polyol (per)fluoropolyether derivative to yield the polyol (per)fluoropolyether derivative.

7 Claims, No Drawings

PROCESS FOR THE MANUFACTURE OF POLYOL PERFLUOROPOLYETHER DERIVATIVE

CROSS-REFERENCE TO RELATED APPLICATIONS

This application is a U.S. national stage application under 35 U.S.C. §371 of International Application No. PCT/EP2008/063278 filed Oct. 3, 2008, which claims priority to European Patent Application No. 07117991.5 filed Oct. 5, 2007, these applications being incorporated herein by reference in their entirety for all purposes.

TECHNICAL FIELD

The invention pertains to a process for the manufacture of polyol perfluoropolyether compounds useful as lubricant for magnetic media.

BACKGROUND ART

As well known, magnetic recording apparatus is divided into those using a magnetic disk as the medium on which to record data and those using magnetic tape as such medium. Because the former type of recording apparatus using a magnetic disk (hereinafter referred to as magnetic disk drives) is prevailing, the following description focuses on magnetic disk drives as an example of the magnetic recording apparatus.

As the capacity enlargement of magnetic disk drives has been pursued for recent years, the fly height of the magnetic head has been lowered rapidly down to below 30 nm, and, consequently, there is increasing need for reliability in terms of resistance to sliding friction.

Also, there is strong need to enhance the data processing speed with more disk capacity. In particular, in a Redundant Array of Independent Disks (RAID) system, a magnetic disk drive that operates at a disk revolving speed of 10,000 rmp or higher is required.

In order to ensure the reliability of a magnetic disk drive, generally, a lubricant layer is formed on a carbon overcoat on the surface of a magnetic disk for use in the disk drive. As the main material of the lubricant layer, usually, fluoropolyether which is a chemically stable fluorinated organic compound is widely used.

Actually, in order to assure reliability of the magnetic disk drive, it is mandatory to efficiently preserve suitable lubricant distribution on the surface of said magnetic disk drive for long operating times. When magnetic disk drives operate, said disk revolves at a high speed and the lubricant might be spun off by the combined action of the air shear due to the air flow on the surface of the disk as the disk revolves, and of the centrifugal force directly exerted on the lubricant. As a consequence, it is often observed that the quantity of the lubricant on the surface of the disk gradually decreases. Also, evaporation phenomena of the lubricant into the atmosphere inside the magnetic drive may take place.

To overcome this problem of the lubricant loss by being spun off during disk revolution and natural evaporation, approaches have heretofore been proposed. Thus, a method for restraining the lubricant from being spun off and evaporated has been proposed in which the adhesion force of the lubricant to the disk protecting layer is made stronger by increasing the polarity of the functional end groups in the lubricant. Said polar end groups are believed to improve adherence of the lubricant to the surface of the magnetic media.

Within this approach, fluoropolyether lubricants based on fluoropolyethers as the backbone and having hydroxyl functional groups as their end groups have shown best performances.

Such materials can be notably manufacture by reaction of epihalohydrins with perfluoropolyether derivatives having two hydroxyl end-group (see Scheme 1 here below), as taught in TURRI, Stefano, et al. End Group Chemistry of Fluoro-Oligomers: Highly Selective Synthese of Diepoxy, Diallyl, and Tetraol Derivatives. (A) *J. polym. sci, A, Polym. chem.* 1996, vol. 34, p. 3263-3275.

Scheme 1

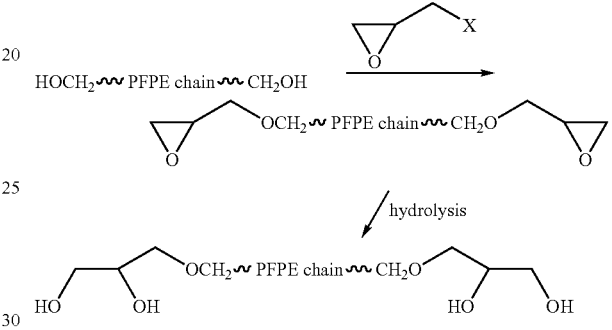

Nevertheless, side reactions are likely to occur during nucleophilic substitution on the epihalohydrin, involving e.g. reactions of oxirane ring with further PFPE hydroxyl derivatives, yielding materials comprising more than one PFPE chain block. Final material thus fails to comply with the expected stoichiometry and fails to possess the targeted anchoring diol functions as end-chains.

Similarly, reaction of perfluoropolyether derivatives having two hydroxyl end-group with glycidol of formula:

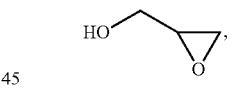

as described in SCHICCHITANO, Massimo, et al. Synthesis and characterization of low-viscosity fluoropolyether-based segmented oligomers. *Die Angewandte Makromoleculare Chemie.* 1995, vol. 231, no. 4000, p. 47-60., yields, in addition to the expected epoxy-substituted derivatives (which can be further converted in corresponding diols), a large range of side-products. As an example, PFPE hydroxyl derivatives can open the oxirane ring of the targeted compound, yielding materials comprising more than one PFPE chain block, and/or, more frequently, a further glycidol molecule can react with the epoxide ring of above mentioned targeted epoxy-substituted intermediate, so that different species are formed.

Mixtures obtained from processes of the prior art are thus generally complex compositions comprising unreacted precursors, targeted polyol derivatives and polymeric material comprising several PFPE chain blocks and/or several ex-glycidol molecules moieties.

Complex purification procedures, based e.g. on supercritical carbon dioxide extraction techniques are thus required for purifying target material, so as to achieve the expected chemical structure and level of functionality at the end groups; said purification steps generate additional burden on manufacturers or users of products obtained as above detailed. Approaches of this type are described, for instance, in US 2004092406 (FUJI ELECTRIC CO LTD (JP)) May 13, 2004, in US 2003100454 (FUJI ELECTRIC CO LTD (JP)) May 29, 2003 and EP 1372141 A (HITACHI LTD (JP)) Dec. 17, 2003.

Also, the synthetic routes sketched herein above suffer for the additional disadvantage that they involve the use of compounds like epihalohydrins and glycidol, whose handling, due to their carcinogenic or suspected carcinogenic behaviour, encounters increasing HSE concerns.

The need was thus felt in the art for a manufacturing process for highly hydroxyl functional perfluoropolyether derivatives having improved selectivity towards targeted compounds, substantially free from side-reactions yielding polymeric derivatives of lower functionality, and not involving the use of toxic (e.g. carcinogenic) reactants.

DISCLOSURE OF INVENTION

It is thus an object of the present invention a process for the manufacture of a polyol (per)fluoropolyether derivative [polyol PFPE (PFPE-OH)], said process comprising:

1. reacting at least one triol having two protected hydroxyl functions and a free hydroxyl group [protected triol (PT)] with an activating agent, to yield an activated protected triol [activated protected triol (APT)];

2. reacting said activated protected triol with a functional (per)fluoropolyether derivative of formula:

$$T_2\text{-O-}R_f\text{-}T_1$$

[functional PFPE (E)], wherein:

$R_f$ represents a fluoropolyoxyalkene chain (chain $R_f$), i.e. a fluorocarbon segment comprising ether linkages in main chain;

$T_1$ and $T_2$, equal to or different from each other, are independently selected from
non-functional groups of formula:

—$CF_3$, —$CF_2$—$CF_3$, —$CF_2Cl$, —$CF_2CF_2Cl$,
—$CF_2$—COF, —COF: and functional hydroxyl groups comprising at least one hydroxyl group, with the provisio that at least one of $T_1$ and $T_2$ is a functional hydroxyl group as above detailed; to yield a protected polyol (per)fluoropolyether derivative [protected polyol PFPE (p-PFPE-OH)];

3. deprotecting said protected polyol PFPE (p-PFPE-OH) to yield the polyol PFPE (PFPE-OH).

The applicant has found that by means of the process of the invention it is possible to manufacture polyol PFPEs (PFPE-OH) having end groups functionalized with hydroxyl moieties with high selectivities and with no involvement of chemicals dangerous for health, said polyol PFPEs (PFPE-OH) being advantageously suitable for use as magnetic lubricants with no need of further purification/separation.

The protected triol (PT) can be notably obtained by reacting a triol [triol (T)] with a protecting agent to yield the protected triol having two hydroxyl functions protected with protective groups and a free, unprotected hydroxyl group.

The terms "protected" and "protective group" have their general meaning and denote chemical modification of the two hydroxyl groups of the triol (T) in order to obtain chemoselectivity in a subsequent chemical reaction towards the free, unprotected hydroxyl group of the protected triol (PT).

Protecting agents for hydroxyl groups are well known in the art. Hydroxyl groups of the triol (T) can be notably protected by transformation in acetals/ketals by reaction with aldehydes or ketones, in corresponding methoxymethyl (MOM) ethers, by reaction with methyl chloromethyl ether (MOM-Cl); p-Methoxybenzyl ethers; Methylthiomethyl ethers; β-Methoxyethoxymethyl ethers, tetrahydropyranyl ethers by reaction with dihydropyran; silyl ethers. Oxetane derivatives (i.e. compounds comprising a four-membered ring with three carbon atoms and one oxygen atom) are also examples of protecting groups for triols (T) having α,α'-hydroxymethyl groups.

Above mentioned protective groups are particularly suitable for the purposes of the invention as they are advantageously stable both against attacks from the activating agent and in the presence of bases and/or nucleophilic agents. This stability enables advantageously protection of these hydroxyl groups during both step 1. and step 2. of the process of the invention, so that the protected hydroxyl groups do not advantageously interfere nor participate in reaction with the activating agent and/or in reaction between the activated group of the activated protected triol (APT) and the functional PFPE (E).

The term triol (T), as used herein, encompasses hydrocarbon compounds having at least three hydroxyl groups.

Compounds having more than three hydroxyl groups can be used with success in the process of the invention, provided that only one reactive hydroxyl group is available for reacting in step 1. of the process of the invention. Nevertheless, it will be preferred to employ compounds having (only) three hydroxyl groups in each molecule.

Non limitative examples of triols (T) are notably:
glycerin of formula:

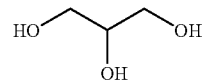

Trimethylolpropane (TMP) of formula:

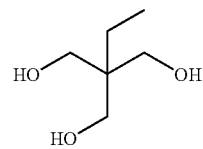

Trimethylolethane (TME) of formula:

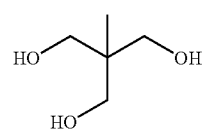

hexane-1,2,6-triol of formula:

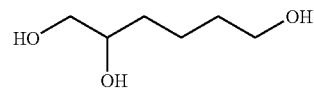

butane-1,2,4-triol of formula:

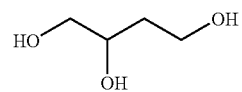

In step 1. of the process of the invention, the protected triol (PT) is reacted with an activating agent as above described to yield the activated protected triol (APT). The term "activated" should be understood to mean that the reaction of the free hydroxyl group of the protected triol (PT) transforms said hydroxyl group into a different functionality which has increased reactivity towards nucleophilic substitution with the functional PFPE (E).

The activating agent suitable for the process of the invention is preferably chosen among:

sulphinyl halides of formula:

wherein X=Cl, Br;

organic sulphonyl halides of formula:

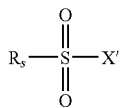

wherein Rs is a $C_1$-$C_{12}$ hydrocarbon radical, linear or branched, optionally fluorinated and X' is Cl or Br;

phosphonyl halides of formula:

wherein X''=Cl, Br.

Non limitative examples of organic sulphonyl halides are notably:

tosyl halides of formula:

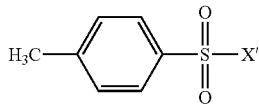

brosyl halides of formula:

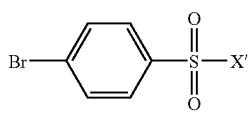

triflyl halides of formula:

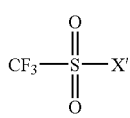

mesyl halides of formula:

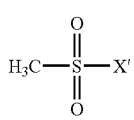

wherein X' in all formulae here above has the same meaning as above detailed.

Generally, step 1. of the process of the invention, is carried out in the presence of a base, preferably of an organic base soluble in the reaction medium.

Non limitative examples of suitable bases are notably trialkyl amines (e.g. triethylamine) and/or heteroaromatic amines (e.g. pyridine).

It is understood that during step 1. of the invention, the protected hydroxyl groups of the protected triol (PT) remain advantageously unchanged, so that the activated protected triol (APT) possesses generally only one activated group.

In step 2. the activated protected triol is reacted with a functional (per)fluoropolyether derivative. Step 2. can be analyzed as a nucleophilic substitution on the activated hydroxyl moiety of the activated protected triol (APT) by the hydroxyl groups of the functional (per)fluoropolyether derivative.

Generally, step 2. of the process of the invention is carried out in the presence of a base, preferably an inorganic base.

As inorganic bases, the following compounds have been used with success:

alkaline and alkaline-earth metal hydroxide, NaOH and KOH being particularly preferred;

metal carbonates, in particular alkaline metal an alkaline-earth metal carbonates, $Na_2CO_3$ and $K_2CO_3$ being particularly preferred.

Organic solvents can be used in step 2. of the process of the invention; generally fluorinated organic solvents are chosen, so that both the functional (per)fluoropolyether derivative and the protected activated triols can be at least partially solubilised. Among fluorinated solvents which have been used with success, mention can be notably made of 1,3-bis(trifluoromethyl)benzene, GALDEN® HT110 and GALDEN® D100 perfluoropolyethers, commercially available from Solvay Solexis S.p.A., HFE 7200 fluoroether, commercially available from 3M, trifluoromethyl benzene (benzotrifluoride) and the like. Also non-fluorinated solvent, like notably acetonitrile, can be used.

Preferred fluorinated organic solvents have generally low miscibility with water (solubility at 23° C. of less than 1% v/v).

Step 2. is thus generally carried out in a biphasic system comprising an aqueous phase. The inorganic base is thus advantageously solubilised in the aqueous phase, while reactants are advantageously solubilised in the organic phase. Generally, suitable phase transfer agents are used; among suitable phase transfer agents, mention can be notably made of tetraalkyl ammonium hydroxides, e.g. tetrabutyl ammonium hydroxide ($TBA^+OH^-$, hereinafter), teramethyl ammonium hydroxide, tetrabutyl ammonium fluoride, tetrabutyl ammonium hydrogen sulphate.

Functional hydroxyl groups of the functional PFPE (E) are preferably selected among groups of formula $-CF_2CH_2O(CH_2CH_2O)_{s'}H$ and $-CF_2CF_2CH_2O(CH_2CH_2O)_{s''}H$, wherein s' and s", equal or different each other and at each occurrence, are integers from 0 to 5; and groups of formula $-CF_2CH_2-O-(CH_2CH_2O)_{w'}E'(OH)_{e'}$, and $-CF_2CF_2CH_2O(CH_2CH_2O)_{w''}E''(OH)_{e''}$, wherein w' and w", equal or different each other and at each occurrence, are integers from 0 to 5, E' and E" are $C_1$÷$C_{12}$ hydrocarbon bridging group; e' and e" are integers from 2 to 4.

More preferably, functional hydroxyl groups of the functional PFPE (E) are chosen among groups of formula $-CF_2CH_2O(CH_2CH_2O)_sH$, as above detailed and groups of formula $-CF_2CH_2O(CH_2CH_2O)_{w'}E'(OH)_{e'}$, as above detailed, in particular those wherein e' is 2 and E' is a $C_1$÷$C_6$ hydrocarbon bridging group.

The fluoropolyoxyalkene chain ($R_f$) of the functional PFPE (E) is preferably a chain comprising repeating units $R°$, said repeating units being chosen among the group consisting of:
(i) —CFXO—, wherein X is F or $CF_3$,
(ii) —CFXCFXO—, wherein X, equal or different at each occurrence, is F or $CF_3$, with the provision that at least one of X is —F,
(iii) —$CF_2CF_2CF_2O$—,
(iv) —$CF_2CF_2CF_2CF_2O$—,
(v) —$(CF_2)_j$—CFZ—O— wherein j is an integer from 0 to 3 and Z is a group of general formula —$OR_f'T_3$, wherein $R_f'$ is a fluoropolyoxyalkene chain comprising a number of repeating units from 0 to 10, said recurring units being chosen among the followings: —CFXO—, —$CF_2CFXO$—, —$CF_2CF_2CF_2O$—, —$CF_2CF_2CF_2CF_2O$—, with each of each of X being independently F or $CF_3$. and $T_3$ being a $C_1$-$C_3$ perfluoroalkyl group.

Thus, the functional PFPE (E) preferably complies with formula (I) here below:

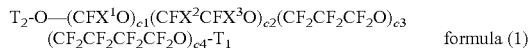

$$T_2\text{-}O\text{---}(CFX^1O)_{c1}(CFX^2CFX^3O)_{c2}(CF_2CF_2CF_2O)_{c3}$$
$$(CF_2CF_2CF_2CF_2O)_{c4}\text{-}T_1 \qquad \text{formula (1)}$$

wherein
$X^1$, $X^2$, $X^3$ equal or different from each other and at each occurrence are independently —F, —$CF_3$;
$T_1$ and $T_2$ are as above defined;
c1, c2, c3, and c4, equal or different from each other, are independently integers $\geq 0$, such that and c1+c2+c3+c4 is in the range 5 to 2000, preferably between 10 and 500; should at least two of c1, c2, c3 and c4 be different from zero, the different recurring units are generally statistically distributed along the chain.

Functional PFPEs (E) suitable for the purposes of the invention can be notably manufactured by photoinitiated oxidative polymerization (photooxidation reaction) of per(halo) fluoromonomers, as described in U.S. Pat. No. 3,442,942 (MONTEDISON SPA) Jun. 6, 1969, U.S. Pat. No. 3,650,928 (MONTEDISON SPA) Mar. 21, 1972, and U.S. Pat. No. 3,665,041 (MONTEDISON SPA) May 23, 1972. Typically, mixtures of perfluoropolyethers can be obtained by combination of hexafluoropropylene and/or tetrafluoroethylene with oxygen at low temperatures, in general below –40° C., under U.V. irradiation, at a wavelength (λ) of less than 3 000 Å. Subsequent conversion of end-groups as described in U.S. Pat. No. 3,847,978 (MONTEDISON SPA) Nov. 12, 1974 and in U.S. Pat. No. 3,810,874 B (MINNESOTA MINING & MFG) Jun. 14, 1974 is notably carried out on crude products from photooxidation reaction. Perfluoropolyether mixtures obtained from such processes are generally available in the form of mixtures of non functional, monofunctional and bifunctional PFPEs.

Non functional PFPEs are those wherein both $T_1$ and $T_2$ are non functional groups as above defined; monofunctional PFPEs are those wherein only one of $T_1$ and $T_2$ is a functional hydroxyl group, as above defined; bifunctional PFPEs are those wherein both $T_1$ and $T_2$ are functional hydroxyl groups.

As an alternative, functional PFPEs can be obtained by fluorination and simultaneous fragmentation of hydrogenated polyethers, like notably polyethylene oxide, as described in U.S. Pat. No. 4,113,772 (CENTRAL GLASS) Sep. 12, 1978 or in U.S. Pat. No. 4,523,039 (THE UNIVERSITY OF TEXAS) Jun. 11, 1985 and subsequent transformation of terminal groups (typically carboxylic acid groups) in corresponding hydroxyl groups.

Still, functional PFPEs can be prepared by ring-opening polymerizing 2,2,3,3-tetrafluorooxethane in the presence of a polymerization initiator to give a polyether comprising repeating units of the formula: —$CH_2CF_2CF_2O$—, and subsequent fluorination of said polyether, as detailed in EP 148482 A (DAIKIN INDUSTRIES) Jul. 17, 1985, or by ionic hexafluoropropylene epoxide oligomerization as described in U.S. Pat. No. 3,242,218 (DU PONT) Dec. 22, 1966. Subsequent conversion of end-groups following procedures detailed herein above for products from photooxidation reaction can be applied here to introduce hydroxyl terminal groups.

The functional PFPE (E) is generally used in the process of the invention as a mixture (M) of non functional, monofunctional and bifunctional PFPEs, i.e. as obtained from above-described processes.

Suitable separation processes have been described in the art, like notably those disclosed in U.S. Pat. No. 5,262,057 (AUSIMONT S.P.A.) Nov. 16, 1993, U.S. Pat. No. 5,910,614 (AUSIMONT S.P.A.) Jun. 8, 1999 and U.S. Pat. No. 5,246,588 (AUSIMONT S.P.A.) Sep. 21, 1993, which enable separating and/or enriching said mixtures in bifunctional PFPEs, so as to obtain a mixture having an increased average functionality, typically an average functionality of at least 1.97.

With the aim of maximizing functionalization degree at the end-groups, it is preferred that the average functionality of the mixture (M) is of at least 1.97, wherein the average functionality is defined as:

$$\frac{(2 \times \text{moles of bifunctional } PFPE + 1 \times \text{moles of monofunctional } PFPE)}{(\text{moles of bifunctional } PFPE + \text{moles of monofunctional } PFPE + \text{moles of nonfunctional } PFPE)}$$

The average functionality of the mixture (M) is of advantageously at least 1.98, preferably of at least 1.985, more preferably of at least 1.99.

Average functionality of the mixture (M) can be determined by $^{19}$F-NMR according to the method described in TURRI, Stefano, et al. NMR of Perfluoropolyether Diols and Their Acetal Copolymers. Macromolecules. 1995, vol. 28, p. 7271-7275.

Deprotection of protected hydroxyl groups derived from activated protected triol in the protected polyol PFPE (p-PFPE-OH) is advantageously carried out in Step 3. of the process of the invention.

The skilled in the art will choose appropriate conditions and reactants for deprotection in step 3. as a function of the protecting groups of the protected triol. Such methods are well known in the art.

Should the hydroxyl groups be protected as acetals/ketals derivatives, hydrolysis in acidic conditions can advantageously provide the targeted polyol PFPE (PFPE-OH).

Should the hydroxyl groups be protected as ether derivatives, acid hydrolysis or hydrogenolysis can advantageously provide the targeted polyol PFPE (PFPE-OH).

By means of the process of the invention is thus possible to obtain polyol (per)fluoropolyether derivatives with high selectivities, which are not contaminated by (per)fluoropolyether side-products, and which can be used with success as such as lubricant of magnetic media.

Still another object of the invention is thus the use for lubricating magnetic media of the polyol PFPEs (PFPE-OH) obtained from the process of the invention.

The present invention will be now described in more detail with reference to the following examples, whose purpose is merely illustrative and not limiting the scope of the invention.

EXAMPLE 1

Preparation of Polyol (Per)Fluoropolyether Derivative (II)

Step. 1 Activation of the protected triol Solketal

The activated protected triol of Solketal (cyclic ketal of glycerin with acetone) of formula:

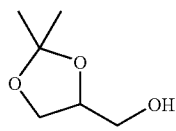

was prepared by reacting Solketal with methansulphonyl-chloride.

A solution of Solketal (100 g, 0.74 eq) in triethylamine (180 g, 1.78 eq) was introduced in a 3-neck round-bottom flask having inner volume of 1 liter, equipped with a magnetic stirring bar, a thermometer and a dropping funnel, and it was maintained at 0-5° C.

A solution of methansulphonylchloride (100 g, 0.85 eq.) in methylene chloride (180 g) was added dropwise to the Solketal solution during 2 hours. At the end of the addition, the temperature was raised to 20° C. and the mixture was washed with demineralized water (3×200 ml).

The organic phase so obtained was separated by extraction and the solvents were removed by distillation under reduced pressure (80° C., 5 mm Hg).

The product was further subjected to vacuum distillation (150° C., $10^{-1}$ mm Hg) to give the mesyl derivative of Solketal (142 g) of formula:

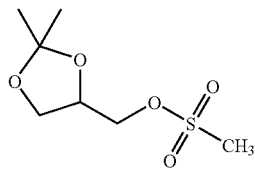

Step. 2 Reaction with Functional PFPE

FOMBLIN® Z-Dol 2000S having formula $HOCH_2CF_2O(CF_2CF_2O)_p(CF_2O)_q\ CF_2CH_2OH$ (p/q=1; p and q were selected so as to obtain MW 2000) (180 g, 0.18 eq), the activated protected triol as above prepared (142 g, 0.68 eq.) and 1,3-bis(trifluoromethyl)benzene (150 ml) were introduced in a 0.5 lt. 3-neck round-bottom flask equipped with a magnetic stirring bar, a bubble cooling pipe and a thermometer.

Potassium hydroxide in powder (16 g, 0.24 eq.) and a 55 wt. % aqueous solution of $TBA^+ OH^-$ (6 g) were added under stirring.

The solution was heated to 70° C. while stirring and kept at this temperature for 8 hours, than it was cooled to 20° C. and washed with demineralized water (3×130 ml). The organic phase was separated by extraction and the fluorinated solvent was removed by distillation under reduced pressure.

The protected polyol (per)fluoropolyether derivative of formula (I) (200 g) was obtained by nucleophilic substitution reaction:

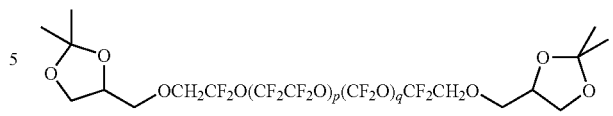

(I)

Step. 3 Deprotection of the Protected polyol (per)fluoropolyether Derivative

Product (I) as above prepared (200 g), methanol (70 ml) and a 25 wt. % aqueous solution of HCl (70 g) were introduced in a 0.5 lt. 3-necked round-bottom flask equipped with a magnetic stirring bar, a bubble cooling pipe and a thermometer.

The solution so obtained was refluxed for 3 hours; the fluorinated heavier phase was separated and the residual solvents were removed by distillation under reduced pressure. As confirmed by $^{19}F$ and $^1H$ NMR analysis, 187 g of a PFPE polyol having formula (II) were obtained:

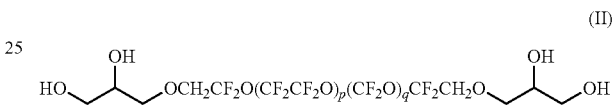

(II)

EXAMPLE 2

Preparation of polyol (per)fluoropolyether Derivative (II)

Similar procedure as detailed in Example 1 was followed but in Step 1. the protected triol Solketal (100 g, 0.74 eq) was activated by reaction with 4-toluensulphonylchloride (160 g, 0.85 eq.) in methylene chloride in the presence of pyridine, so as to obtain 142 g of the corresponding activated protected diol of formula:

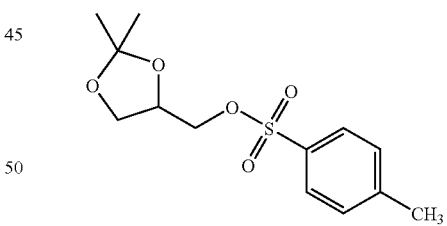

Steps 2. and 3. were carried out as described in Example 1 and yielded strictly similar results.

EXAMPLE 3

Preparation of polyol (per)fluoropolyether Derivative (II)

Similar procedure as detailed in Example 2 was followed but in Step 2., powdered potassium hydroxide was replaced by powdered potassium carbonate (72 g, 0.54 eq.), reaction temperature was raised to 80° C. and reaction time to 12 h.

200 g of product (I) were obtained. Step 3. was carried out as described in Example 1. and yielded strictly similar results.

EXAMPLE 4

Preparation of polyol (per)fluoropolyether Derivative (IV)

Similar procedure as detailed in Example 1 was followed but the protected triol used in Step 1. was (2,2-dimethyl-1,3-dioxan-5-yl)methanol (100 g, 0.74 eq) in triethylamine (180 g, 1.78 eq), instead of Solketal.
Step 2. Thus yielded product having formula (III) (200 g):

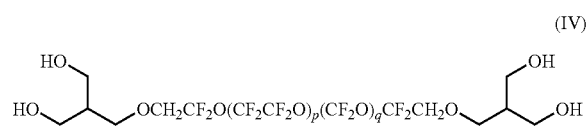

(III)

The PFPE tetraol having formula (IV) (187 g) was obtained by deprotecting the product (III) in Step 3. following same procedure as detailed in example 1:

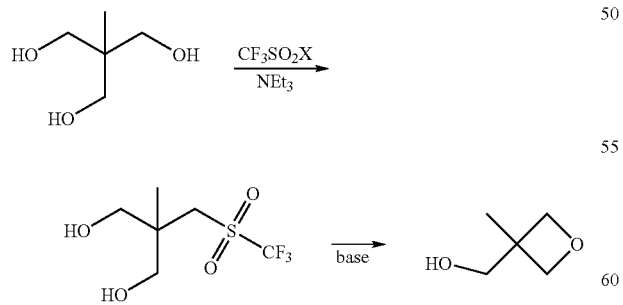

(IV)

EXAMPLE 5

Preparation of polyol (per)fluoropolyether Derivative (VI)

Step 0. Synthesis of the Protected triol
1,1,1 tris(hydroxymethyl)ethane (1 mole) was reacted with $CF_3SO_2X$ (1 mole) to yield the corresponding compound having one hydroxyl groups converted in triflic group, which was isolated by fractional distillation. Cyclic oxetane derivative was obtained by internal nucleophilic displacement of the triflate by a hydroxyl group in the presence of a base in diluted conditions (0.1-0.5 M). The methyl-hydroxymethyl-oxetane was isolated after elimination of solvents and purification.

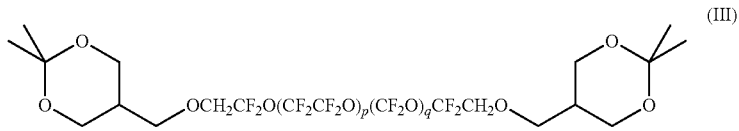

Step. 1 Activation of the Protected triol oxetane
The methyl-hydroxymethyl-oxetane obtained as above described was reacted with 1 eq. mol of triflyc halide following procedure described in example 1, as shown in the following reaction scheme:

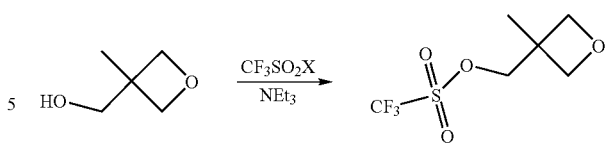

Step 2.
FOMBLIN® Z-DOL (180 g, 18 eq) and the triflyc oxethane obtained from Step 1. (0.54 eq.) were introduced in a 0.5 lt. 3-neck round-bottom flask equipped with a magnetic stirring bar, a bubble cooling pipe and a thermometer.

A 50 wt. % aqueous solution of NaOH (130 g, 1.62 eq.) and a 55 wt. % aqueous solution of $TBA^+ OH^-$ (6 g) were added under stirring.

The solution was heated to 60° C. while stirring and kept at this temperature for 8 hours. The organic phase was separated by extraction and the excess of oxetane derivative was removed by distillation under reduced pressure. Product having formula (V) (190 g) was obtained:

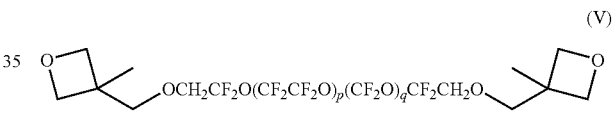

(V)

Step 3.
The PFPE tetraol having formula (VI) (190 g) was obtained by deprotecting the intermediate product (V) (200 g) in the presence of methanol (70 ml) and of a 10 wt. % aqueous solution of $HClO_4$ (70 g) at 60° C. for 5 hours:

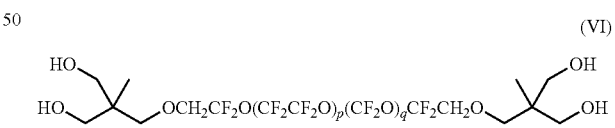

(VI)

EXAMPLE 6

Preparation of polyol (per)fluoropolyether Derivative (XII)

Similar procedure as detailed in Example 1 was followed but in Step 2. the polyol PFPE derivative of formula (II) (90 g, 0.18 eq.) was used instead of FOMBLIN® Z-Dol.

Product having formula (XI) (100 g) was obtained by the nucleophilic substitution reaction:

are integers from 0 to 5; and groups of formula —$CF_2CH_2O(CH_2CH_2O)_{w'}E'(OH)_{e'}$, and —$CF_2CF_2CH_2O(CH_2O)_{w''}E''(OH)_{e''}$, wherein w' and w", equal to or different from each other and at each occurrence, are integers from 0 to 5; E' and E" are $C_1$-$C_{12}$ hydrocarbon bridging group; and e' and e" are integers from 2 to 4.

(XI)

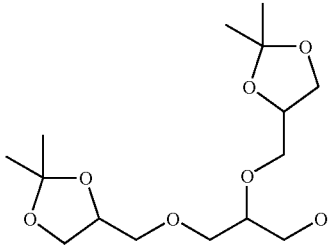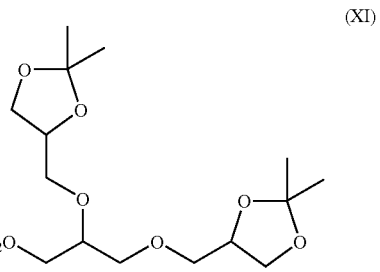

Step 3. The PFPE tetraol having formula (XII) (95 g) was obtained by deprotecting the product (XI) (200 g) in the presence of methanol (100 ml) and of a 25 wt. % aqueous solution of HCl (50 g):

(XII)

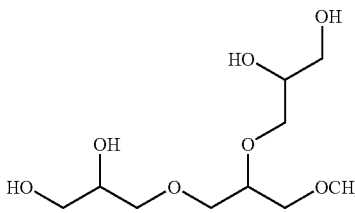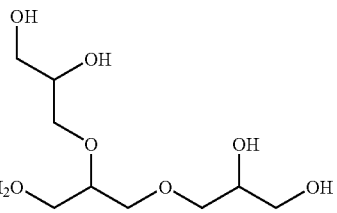

The invention claimed is:

1. A process for the manufacture of a polyol (per)fluoropolyether derivative [polyol PFPE (PFPE-OH)], said process comprising:
   1 reacting at least one triol having two protected hydroxyl functions and a free hydroxyl group [protected triol (PT)] with an activating agent, to yield an activated protected triol [activated protected triol (APT)];
   2 reacting said activated protected triol with a functional (per)fluoropolyether derivative of formula:

$T_2$—O—$R_f$—$T_1$

[functional PFPE (E)], wherein:
   $R_f$ represents a fluoropolyoxyalkene chain (chain $R_f$), said chain $R_f$ being a fluorocarbon segment comprising ether linkages in main chain;
   $T_1$ and $T_2$, equal to or different from each other, are independently selected from the group consisting of non-functional groups of formula:

—$CF_3$, —$CF_2$—$CF_3$, —$CF_2Cl$, —$CF_2CF_2Cl$, —$CF_2$—COF, —COF: and functional hydroxyl groups comprising at least one hydroxyl group, with the provisio that at least one of $T_1$ and $T_2$ is a functional hydroxyl group as above detailed;
   to yield a protected polyol (per)fluoropolyether derivative [protected polyol PFPE (p-PFPE-OH)]; and
   3 deprotecting said protected polyol PFPE (p-PFPE-OH) to yield the polyol PFPE (PFPE-OH).

2. The process of claim 1, wherein the functional hydroxyl groups of the functional PFPE (E) are selected from the group consisting of groups of formula —$CF_2CH_2O(CH_2CH_2O)_{s'}H$ and —$CF_2CF_2CH_2O(CH_2CH_2O)_{s''}H$, wherein s' and s", equal to or different from each other and at each occurrence, 3. The process of claim 2, wherein the functional hydroxyl groups of the functional PFPE (E) are selected from the group consisting of groups of formula —$CF_2CH_2O(CH_2CH_2O)_{s'}H$, as defined in claim 2 and groups of formula —$CF_2CH_2O(CH_2CH_2O)_{w'}E'(OH)_{e'}$, as defined in claim 2.

4. The process according to claim 1, wherein the fluoropolyoxyalkene chain ($R_f$) of the functional PFPE (E) is a chain comprising repeating units $R°$, said repeating units being selected from the group consisting of:
   (i) —CFXO—, wherein X is F or $CF_3$,
   (ii) —CFXCFXO—, wherein X, equal to or different from each other at each occurrence, is F or $CF_3$, with the provision that at least one of X is —F,
   (iii) —$CF_2CF_2CF_2O$—,
   (iv) —$CF_2CF_2CF_2CF_2O$—, and
   (v) —$(CF_2)_j$—CFZ—O— wherein j is an integer from 0 to 3, and Z is a group of general formula —$OR_f'T_3$, wherein $R_f'$ is a fluoropolyoxyalkene chain comprising a number of repeating units from 0 to 10, said recurring units being selected from the group consisting of: —CFXO—, —$CF_2CFXO$—, —$CF_2CF_2CF_2O$—, and —$CF_2CF_2CF_2CF_2O$—, with X being independently F or $CF_3$, and $T_3$ being a $C_1$-$C_3$ perfluoroalkyl group.

5. The process according to claim 1, wherein the functional PFPE (E) complies with formula (1):

$T_2$—O—$(CFX^1O)_{c1}(CFX^2CFX^3O)_{c2}(CF_2CF_2CF_2O)_{c3}(CF_2CF_2CF_2CF_2O)_{c4}$-$T_1$ wherein
   $X^1, X^2, X^3$ equal to or different from each other and at each occurrence are independently —F, or —$CF_3$;
   $T_1$ and $T_2$ are as defined in claim 1;
   c1, c2, c3, and c4, equal to or different from each other, are independently integers $\geq 0$, such that c1+c2+c3+c4 is in the range 5 to 2000.

6. The process according to claim 1, wherein the activating agent is selected from the group consisting of:

sulphinyl halides of formula:

$$SO_2X$$

wherein X=Cl, or Br;

organic sulphonyl halides of formula:

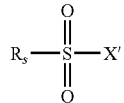

wherein Rs is a $C_1$-$C_{12}$ hydrocarbon radical, linear or branched, optionally fluorinated and X' is Cl or Br; and phosphonyl halides of formula:

$$PX''_3$$

wherein X" =Cl, or Br.

7. A method for lubricating magnetic media comprising:
manufacturing a polyol (per)fluoropolyether derivative [polyol PFPE (PFPE-OH)] according to the process of claim 1; and
applying the manufactured polyol (per)fluoropolyether derivative (PFPE-OH) to a surface of the magnetic media.

\* \* \* \* \*